(12) United States Patent
Vallgren et al.

(10) Patent No.: US 11,185,297 B2
(45) Date of Patent: Nov. 30, 2021

(54) DETECTOR MODULE SYSTEM AND MEDICAL APPARATUS FOR POSITRON EMISSION TOMOGRAPHY

(71) Applicant: Terapet Ltd., Geneva (CH)

(72) Inventors: Christina Vallgren, Arzier-le Muids (CH); Marcus Palm, Arzier-le Muids (CH)

(73) Assignee: TERAPET LTD., Geneva (CH)

( * ) Notice: Subject to any disclaimer, the term of this patent is extended or adjusted under 35 U.S.C. 154(b) by 0 days.

(21) Appl. No.: 17/288,646

(22) PCT Filed: Oct. 25, 2019

(86) PCT No.: PCT/EP2019/079249
§ 371 (c)(1),
(2) Date: Apr. 26, 2021

(87) PCT Pub. No.: WO2020/084139
PCT Pub. Date: Apr. 30, 2020

(65) Prior Publication Data
US 2021/0307708 A1 Oct. 7, 2021

(30) Foreign Application Priority Data

Oct. 25, 2018 (EP) .................................... 18202581

(51) Int. Cl.
*A61B 6/00* (2006.01)
*A61B 6/03* (2006.01)
*G01T 1/29* (2006.01)

(52) U.S. Cl.
CPC ............ *A61B 6/4266* (2013.01); *A61B 6/037* (2013.01); *A61B 6/4411* (2013.01);
(Continued)

(58) Field of Classification Search
CPC ... G01T 1/2985; A61B 6/4266; A61B 6/4411; A61B 6/508; A61B 6/4494; A61B 6/037
See application file for complete search history.

(56) References Cited

U.S. PATENT DOCUMENTS 9,910,161 B1 * 3/2018 Tonami ................. G01T 1/2018
2010/0078566 A1 4/2010 Moor
(Continued)

FOREIGN PATENT DOCUMENTS

WO 2015124023 A1 8/2015

OTHER PUBLICATIONS

European Search Report issued in corresponding Patent Application No. 18202581.7 dated Mar. 20, 2019.
(Continued)

*Primary Examiner* — Michael C Bryant
(74) *Attorney, Agent, or Firm* — Buchanan Ingersoll & Rooney P.C.

(57) ABSTRACT

A detector module system for positron emission tomography including a plurality of gamma ray detector modules. Each pair of one detector module and one interconnection element includes mutually engaging locking means for releasably connecting the detector module to the interconnection element. Further each interconnection element includes locking means for releasably connecting at least two detector modules to said interconnection element. Further each of said gamma ray detector modules includes a sensor adapted to detect gamma radiation occurring from short-lived radionuclides radiating from a body and to generate a radiation output corresponding to the detected gamma radiation, and the detector module system comprises a processing circuitry adapted to receive said radiation output from each of the gamma ray detector modules and to generate a resulting radiation representation for the positron emission tomogra-
(Continued)

phy event, based on the received radiation output. Also, a medical apparatus for positron emission tomography.

8 Claims, 10 Drawing Sheets

(52) U.S. Cl.
CPC ............ *A61B 6/4494* (2013.01); *A61B 6/508* (2013.01); *G01T 1/2985* (2013.01)

(56) References Cited

U.S. PATENT DOCUMENTS

| | | |
|---|---|---|
| 2011/0297833 A1 | 12/2011 | Takayama |
| 2012/0112078 A1* | 5/2012 | Millett .................. G01T 1/2985 250/363.03 |
| 2014/0185744 A1* | 7/2014 | Zhang .................. G01N 23/046 378/10 |
| 2016/0187496 A1* | 6/2016 | Bradford ............... G01T 1/2985 250/366 |
| 2016/0270744 A1 | 9/2016 | Sachs et al. |
| 2017/0014646 A1 | 1/2017 | Lee et al. |

OTHER PUBLICATIONS

International Preliminary Report on Patentability (PCT/IPEA/409) dated Feb. 8, 2021, by the European Patent Office as the International Searching Authority for International Application PCT/EP2019/079249.

International Search Report (PCT/ISA/210) and Written Opinion (PCT/ISA/237) dated Jan. 30, 2020, by the European Patent Office as the International Searching Authority for International Application No. PCT/EP2019/079249.

Second Written Opinion (PCT/IPEA/408) dated Oct. 6, 2020, by the European Patent Office as the International Search Authority for International Application No. PCT/EP/2019/079249.

* cited by examiner

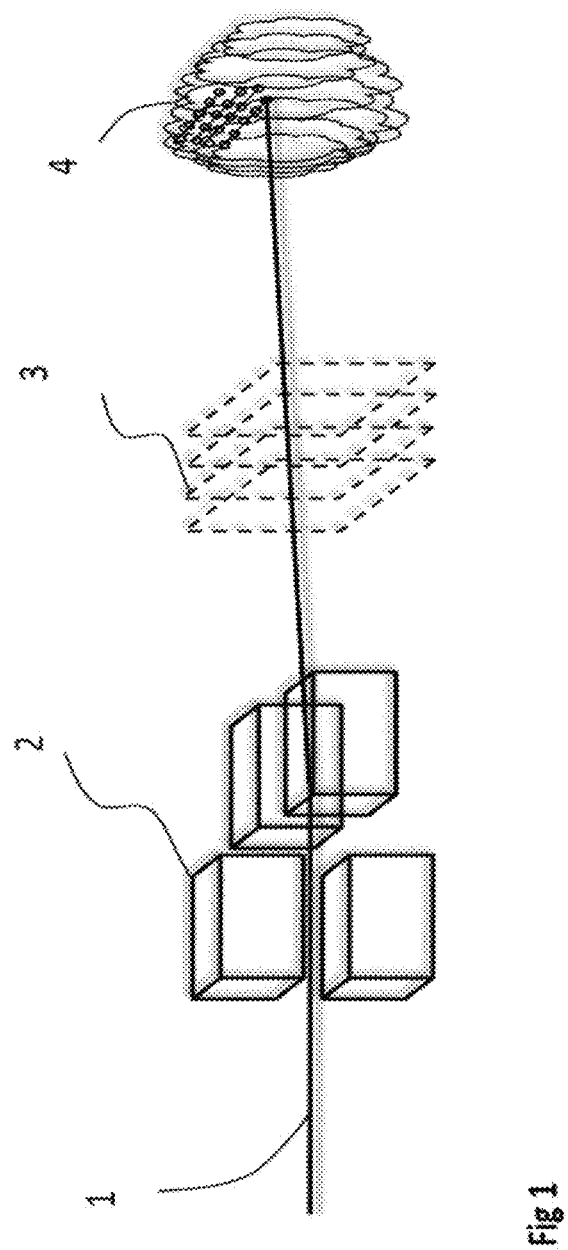

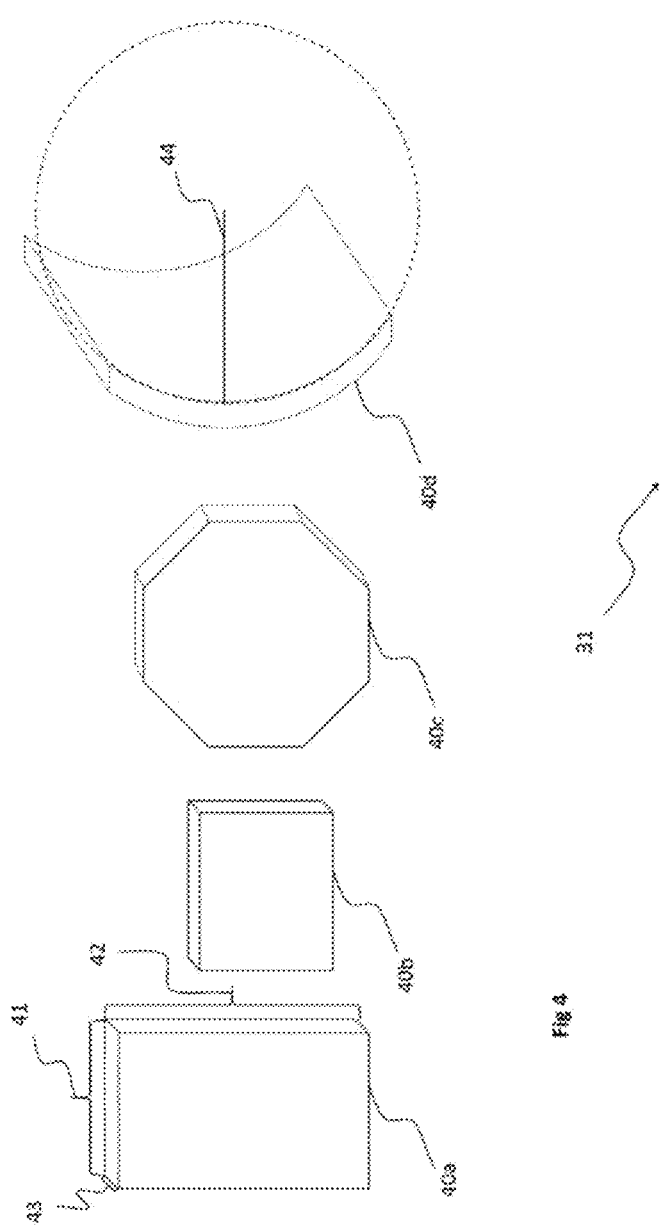

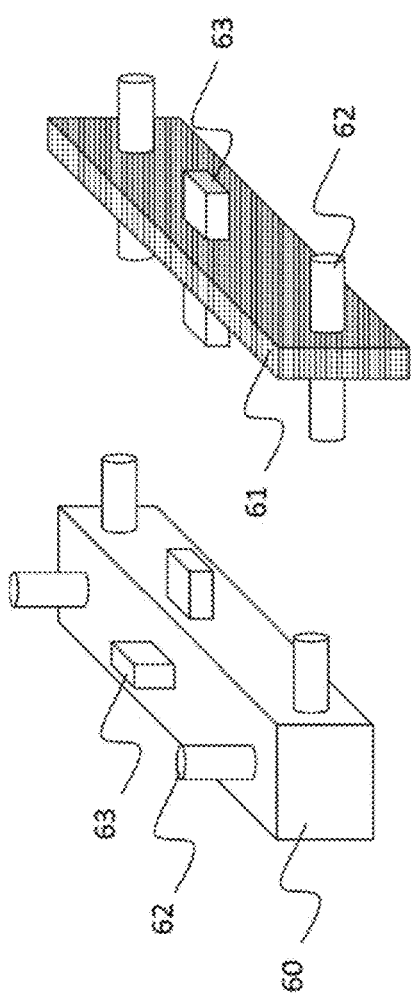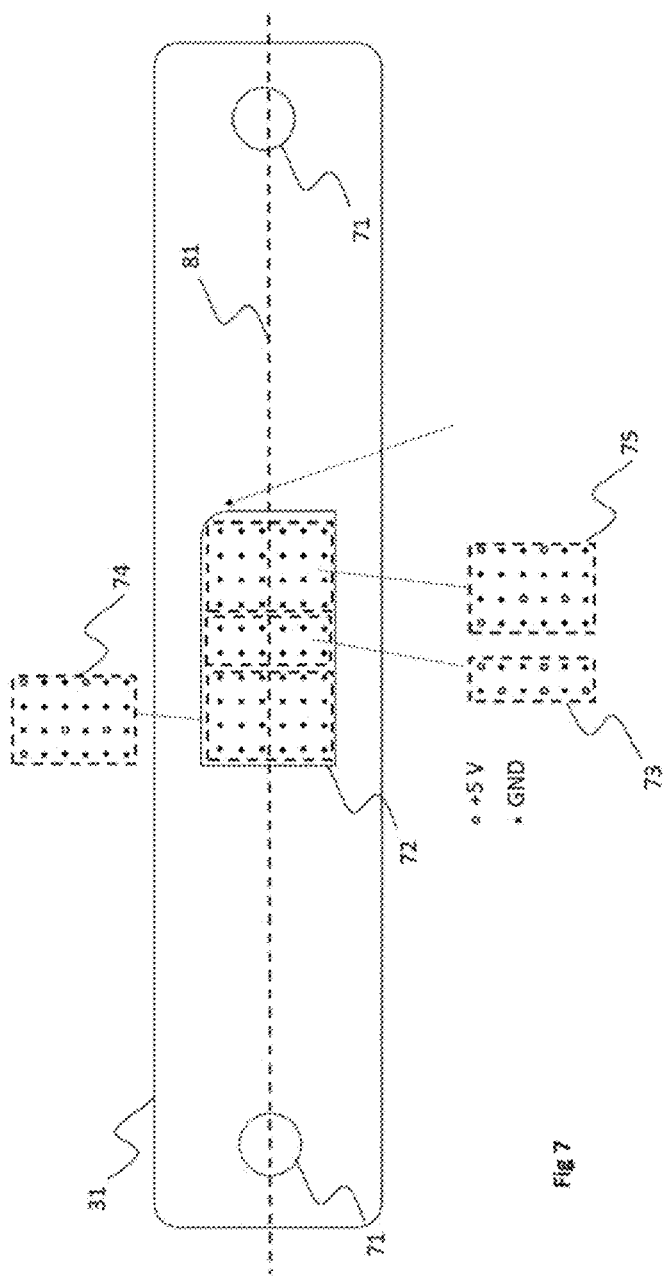

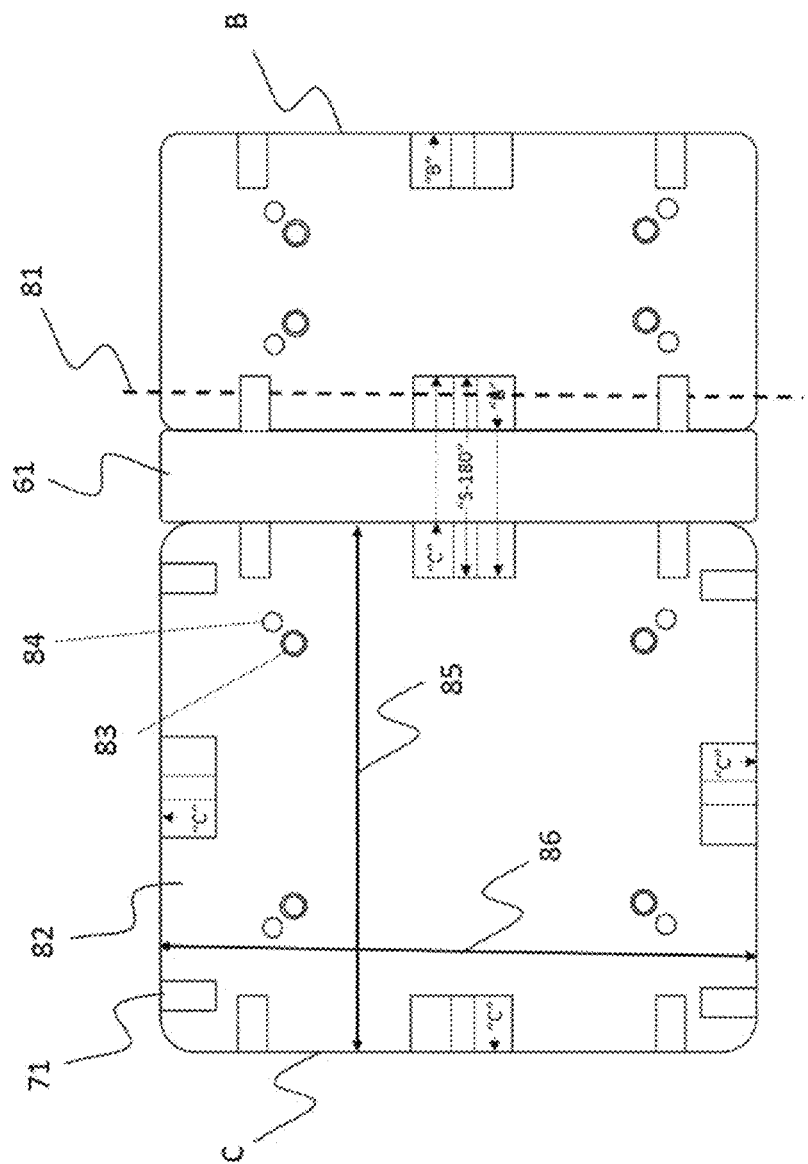

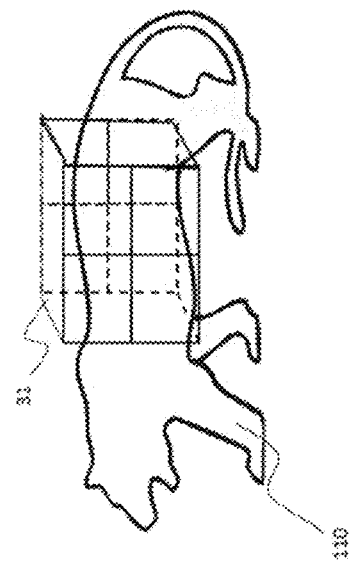
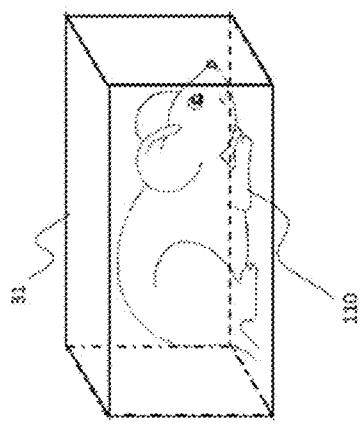
Fig 11
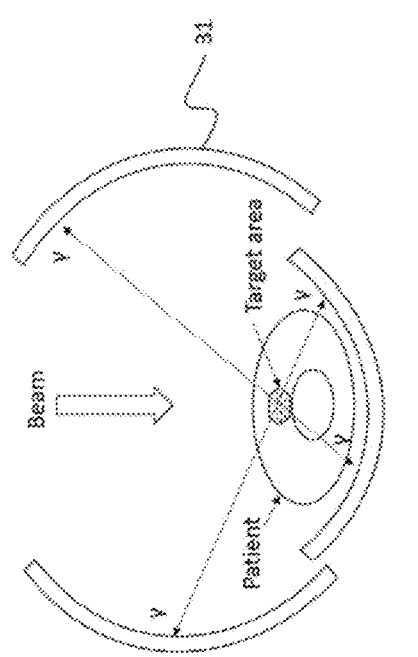
Fig 10B
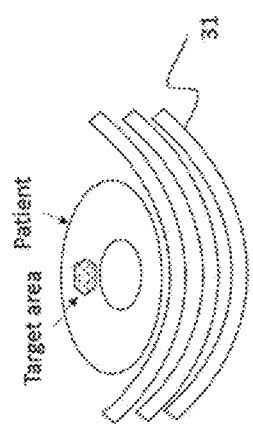
Fig 10A

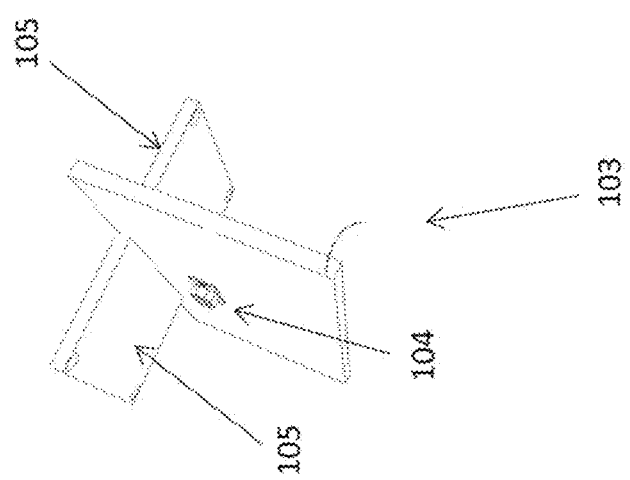
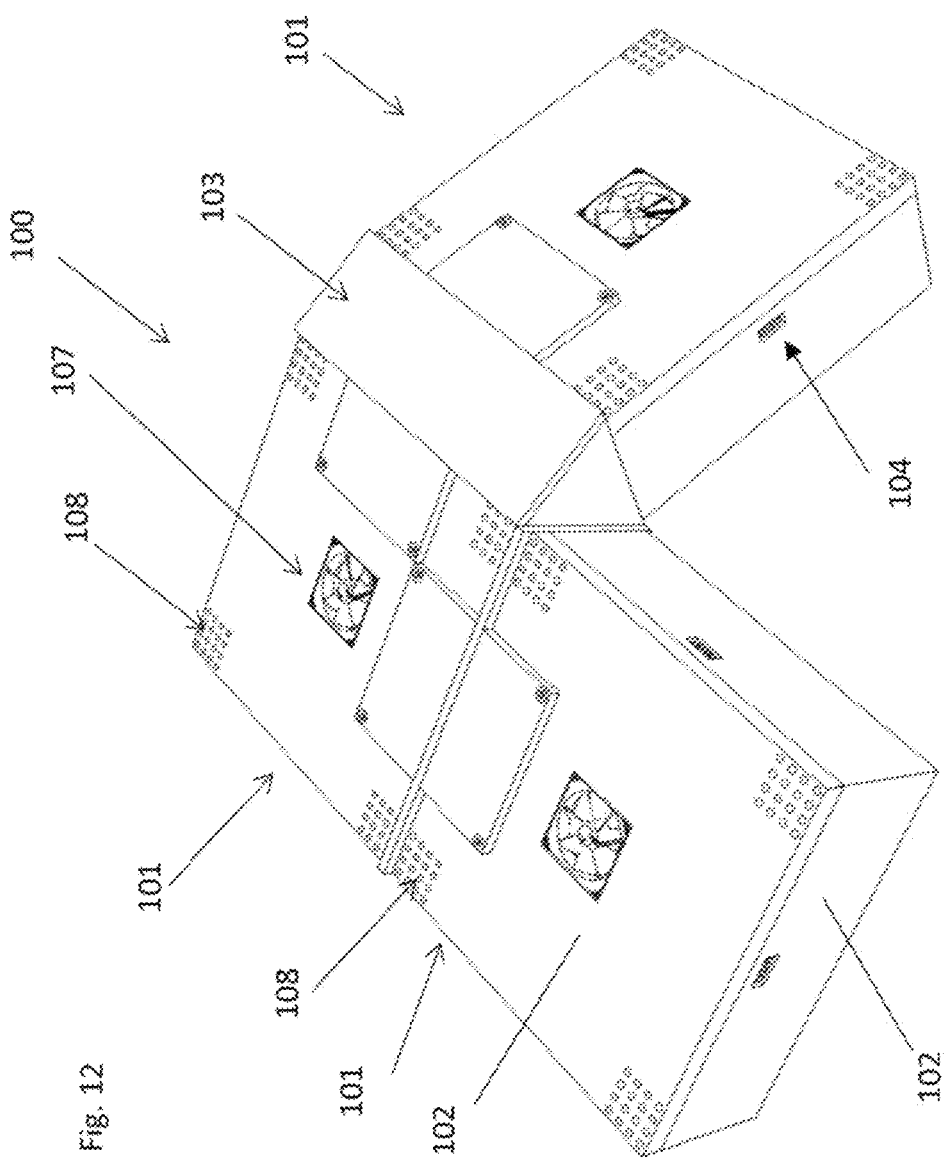

DETECTOR MODULE SYSTEM AND MEDICAL APPARATUS FOR POSITRON EMISSION TOMOGRAPHY

TECHNICAL FIELD OF THE INVENTION

The present invention relates to a detector module system and further to a medical apparatus for positron emission tomography scan.

BACKGROUND OF THE INVENTION

Positron emission tomography (PET) is an imaging technology widely used today. One particular use case for PET scanning is to visualize the penetration depth of an irradiating beam e.g. an ion beam. When using an ion beam to irradiate e.g. a body part of a patient, the penetration depth of the beam in the patient can be uncertain e.g. due to tissue heterogeneities, patient mis-positioning, or uncertainties in stopping power, and safety margins must be employed to spare critical organs from dose and/or ensuring sufficient dose is given to the entire target area. A PET scan can give information on exactly where in the patient dose has been deposited.

However, there are practical and technical issues with using conventional PET scanners.

At many of today's ion beam centres, the following PET scanning methods are applied. Off-line PET: the measurement starts with time delays of several minutes after ion beam irradiation, the patient is transported to a conventional PET system usually combined with computer tomography (CT) scanning. In this approach the imaging is carried out at a remote site and there is a relatively long delay for PET acquisitions. Further, the short-lived radionuclide species have decayed and only the activity of long half-life radio-isotopes generated by the ion beam is detected. The performance is further degraded by the biological washout of the ion beam induced PET activity, which reduces the activity level in the target region.

In an alternative approach, in-room PET, the measurement takes place shortly after irradiation with a PET scanner located in the same room as the ion beam system. With this approach, the time lost between irradiation and start of PET scan is reduced. However, the downsides include at least the extra cost of a stand-alone PET scanner and extra occupation time in the irradiation room. Therefore, there is need in the field to develop versatile and cost-effective PET scanning systems.

U.S. Pat. No. 9,910,161 B1 discloses a radiation detector applied to a combined apparatus for positron emission tomography and magnetic resonance tomography to obtain a nuclear medicine image and a magnetic resonance image at the same time US 2012/112078 A1 discloses a. imaging system, and more specifically to a mobile imaging system for medical diagnosis.

SUMMARY OF THE INVENTION

It is accordingly an object of the present invention to alleviate all or at least some of the above-mentioned drawbacks known in the field.

This object and other objects are achieved by providing a detector module system and a medical apparatus for positron emission tomography as defined in the appended claims.

The term exemplary is in the present context to be understood as serving as an example, instance or illustration.

According to a first aspect of the present invention there is provided a medical apparatus for positron emission tomography, the medical apparatus comprising:

a plurality of individual gamma ray detector modules, wherein the plurality of individual gamma ray detector modules comprises a first, a second and a third gamma ray detector module each of the first, second and third gamma ray detector modules being adapted to be arranged on a respective side of an animal or human body during a positron emission tomography event, and each of the modules being adapted to detect gamma radiation occurring from short-lived radionuclides radiating from at least one portion of the animal or human body and to generate a radiation output corresponding to the detected gamma radiation, wherein the first and second detector modules are arranged on opposite sides of the animal or human body, and the surface normals to the first and second gamma ray detector modules are all parallel with a first geometrical plane, and at least one normal to the third gamma ray detector module is transverse to the first geometrical plane;

a processing circuitry adapted to receive the radiation output from each of the individual gamma ray detector modules and to generate a resulting radiation representation for the positron emission tomography event, based on the received radiation output.

According to a second aspect of the present invention there is provided a medical apparatus for positron emission tomography, the medical apparatus comprising:

a plurality of individual gamma ray detector modules, wherein the plurality of individual gamma ray detector modules comprises a first, and a second gamma ray detector module each of the first, and second gamma ray detector modules being adapted to be arranged on a respective side of an animal or human body during a positron emission tomography event, and each of the modules being adapted to detect gamma radiation occurring from short-lived radionuclides radiating from at least one portion of the animal or human body and to generate a radiation output corresponding to the detected gamma radiation, wherein the first and second detector modules are preferably arranged on opposite sides of the animal or human body, and the surface normals to the first and second gamma ray detector modules are all parallel with a first geometrical plane;

a processing circuitry adapted to receive the radiation output from each of the individual gamma ray detector modules and to generate a resulting radiation representation for the positron emission tomography event, based on the received radiation output.

The inventors have realized that providing a PET scanner with individual gamma ray detector modules, sometimes also referred to as "detector modules" or "modules" hereinafter, allows for a versatile and easy-to-integrate PET scanning system where the detector modules can be assembled and/or disassembled before, during and after a positron emission tomography event or positron emission tomography scanning session, these terms are used interchangeably. A positron emission tomography scanning session may sometimes also be referred to as a PET session or PET scanning session in the rest of this description.

When the medical apparatus comprises only two detector modules these are preferably but not necessarily arranged on opposite sides of the animal or human body.

In relation to this invention the term positron emission tomography event or a PET session denotes a period of time within which at least one detector module detects a radiation input and generates a radiation output, optionally including that a radiation representation is generated based on the output from a plurality of detector modules.

An advantage of the modular system is that it can be readily integrated with e.g. a second imaging or irradiation system such as an ion beam system. The modular PET scanner allows the ion beam to reach the subject, e.g. a body of a patient or animal under the scanner unobstructed while permitting gamma rays from positron annihilation inside the patient to be detected by the detector modules. Another advantage of this modular PET scanner is that the individual gamma ray detection modules can be assembled in a customizable manner to the requirements of the PETscanning session. In other words, the modular gamma ray detectors can be arranged in various outlines in the close proximity of the body parts or tissues that are to undergo the PET scanning. The detectors can be assembled according to the size and shape of the subject, the physical location of the irradiation volume e.g. head, abdomen, etc., the orientation of the subject under PET scanning e.g. a sitting or standing patient, the spatial arrangement and geometrical constraints of the surrounding equipment e.g. a rotating gantry or an ion beam delivery nozzle from a fixed ion beam line.

The modules may be assembled without a supporting frame or be a part of a PET scanner frame. The gamma ray detector modules may be placed on, or entirely or partially integrated with, the same bed or couch as the patient is placed on, and may therefore move together with the patient whenever the table/couch is moved. Thus, no re-positioning of the detectors may be necessary if the penetration direction of the beam is changed during the operation of the system. The individual gamma ray detector modules may be placed directly on the subject e.g. a body part of the patient. Thanks to the modular design, the individual detectors may have a variety of shapes, sizes, curvatures, etc. The individual detectors may be mechanically rigid or flexible. The individual detectors may have a symmetrical or asymmetrical geometry such a circular, rectangular, tubular, hemispherical, cylindrical, etc. outline or be of any irregular and customized shape.

With the inventive concept, no modification of existing beam delivery equipment, such as a fixed beam delivery nozzle or gantry, is required. Further, the compact size allows the device to be used in combination with a gantry where space is limited. Additionally, a PET scan can be performed during the beam delivery sequence without the need to transport or re-position the patient for a post-irradiation PET scan. Even more advantageously, real-time monitoring of the penetration depth can allow for feedback correction and/or beam interruption, if e.g. the measured penetration depth deviates from a planned penetration depth. In the same context, the data from the device—the spatial distribution of the detected positron annihilation activity—may be used in combination with the predicted positron annihilation activity. The predicted activity can be modeled based on cross sections for different nuclear interaction between the beam and the different tissues along the beam path. By comparing the measured positron annihilation activity with the prediction, it is possible to—during the PET scanning session—detect if e.g. the actual penetration depth of the beam deviates from the planned depth.

The inventors have realized that by arranging the PET detectors in three dimensions, where at least two of the detectors, the first detector and the second detector, are arranged on opposite sides of the portion (also may be referred to as target area) of the animal or human body, the normal of these detectors expand such that they are parallel to a plane. This plane is a geometrical imaginary plane and is perceived to be transverse to at least one of the first or second PET detectors arranged on the opposite sides of e.g. the patient. When a third detector is arranged in the proximity of the portion of the patient's body it is arranged such that a normal of the third detector is transverse to the imaginary geometrical plane. Thus a three-dimensional coverage is achieved around the portion of the patient's body subjected to a PET session. It should be appreciated that the spatial position, orientation, angles, and directions of the detector modules can be adjusted and changed by the user during, before or after the PET session in a manual or automated way.

The radiation output generated from each of the individual gamma ray detectors may correspond to the energy of the detected gamma radiation for each detector during the positron emission tomography event. By combining the received irradiation output from each of the individual gamma ray detectors the processing circuitry may generate a radiation representation for the PET session.

The processing circuitry may process data from all PET/gamma ray modules related to detection events including time-stamps and spatial information i.e. absorption segment.

The processing circuitry may comprise a plurality of central processing units (CPUs) or graphical processing units (GPUs) working in parallel.

Prior to operation, the processing circuitry may be provided with information on how the different modules are oriented in space, in order to accurately reconstruct ray paths of coincidence events.

During operation, the processing circuitry may process the incoming data from the connected detector modules and construct images corresponding to the measured PET activity within the field-of-view of the detector modules. Prior to operation, the processing circuitry may also have been provided data to perform attenuation correction e.g. CT/MRI-based calibration data on the images.

The radiation representation generated by the processing circuitry may be in form of a data file, a log report, a graphical display-readable data file presented to a user of the medical apparatus on a screen, or the like. This radiation representation may be communicated out of the medical apparatus to a local or remote file storage unit, a local or remote processor unit, a local or remote controller machine, a designated processing software program being operated on a computing machine, etc. for storage, further processing or creating control instruction purposes. The radiation representation data files can also be communicated to user devices with user software applications. The processing circuitry may be a centralized machine comprising a plurality of processing machines or may be a distributed processing machine with a plurality of processors. The processing circuitry of the medical apparatus may be realized wholly or partly in hardware. However, the processing circuitry may alternatively be realized as software-controlled processing circuitry. For example, the processing circuitry may be realized as a plurality of computer processing units that together form the processing circuitry i.e. a plurality of computers may be interconnected in order to form the processing circuitry and its functionality in the context of the present invention.

In accordance with an exemplary embodiment of the present invention, each individual gamma ray detector module may further comprise a processor unit configured to generate and send the radiation output of each individual gamma ray detector module to the processing circuitry.

The processor unit of course can comprise more than one processor or a plurality of distributed processors or a plurality of centralized processors. The processor unit may also send and/or receive the radiation output to and/or from other individual detector modules.

The processor unit may send and/or receive a spatial position or angle of each detector to the processing circuitry or to the processor units of the other individual detector modules. The processor unit may further send any data associated with the gamma absorption such as detection time of a measurement event or a period of a measurement event, the energy of the detected radiation output, signal shape of the radiation output, amplitude of the radiation output, etc. to the processing circuitry or other detector modules.

Another advantage of having a processor unit with each gamma ray detector module is that, information generated during a PET scanning session can be locally recorded and processed by each individual gamma ray detector module. This in turn may ease the requirements of heavy data processing on a central processing circuitry or computing machine arranged to receive all the raw data e.g. radiation output from the detector modules and perform a heavy processing at a single step. Alternatively, when the processing of the measurement and/or scanning recordings is operated by individual processor units of each detector, the processing circuitry may be tasked with reconstructing the processed data and generate a complete graphical and/or analytical result of the PET scanning session. Further, the detector modules may comprise a communicating network interface configured to link the processor units of the individual gamma ray detector modules and/or the processing circuitry to send and/or receive data or instructions.

In accordance with an exemplary embodiment of the present invention, the processing circuitry may further be configured to generate and send control instructions to said detector modules to control a position and/or orientation of said detector modules.

The processing circuitry may further generate and send instruction to individual gamma ray detectors to control the position, orientation, angle or direction of the detector modules. The user of the medical apparatus can adjust the position or orientation of the detectors by entering the control commands to the system via a data entry module. The control instructions may be automatically generated by the processing circuitry based on the data received from the processor units of the detector modules on the position, angle or any other associated information with the PET scanning session such as the detected energy of the radiation by the detector modules.

In accordance with one exemplary embodiment of the present invention, the control instructions may further comprise a deactivation instruction to deactivate and/or disable functionality of at least one of the plurality of individual gamma ray detector modules during parts of the PET scanning session.

During, before or after the PET scanning session individual modules can be deactivated and/or disabled. The position or orientation of the modules can also be changed such that e.g. certain modules are moved out of the ion beam path for example by folding the modules or by placing the modules in a resting/idle status or position. Disabled modules may not acquire any radiation detection data. This provides flexibility to the user, e.g. during the PET session if any adjustments to the process become necessary.

The control instructions may be sent to the detector modules via a local communication network and/or a wide area network or through web-based software applications.

The processing circuitry may send data and control instructions to individual detector modules through communication links stablished by using the GSM, satellite, WIFI, Bluetooth, or any other local communication interfaces.

The processor units of individual gamma ray detectors may send and/or receive spatial and/or temporal information of the individual gamma ray detector modules to and/or from the processing circuitry. In other words, during a PET scanning session the processing circuitry has real-time communication with each individual detector and e.g. can send a request to acquire certain information about the angle, orientation, position with respect to other detectors or position with respect to e.g. ion beam nozzle, etc. Additionally, the processor unit of each individual gamma ray detector may be in real-time communication with the other processor units of the plurality of individual gamma ray detector modules. Each detector module can thus be updated with real-time spatial and/or temporal data of other detector modules during a PET scanning session. Such information may also be utilized to reconfigure the detectors off-line i.e. before or after a PET scanning session. This can be advantageous e.g. in circumstances where a PET scanning session has been interrupted due to a detected deviation of the ion beam penetration depth from a predetermined planned depth of penetration. This information can also be used in real-time to adjust a position of a detector or energy or direction of the ion beam. In some embodiments a stand-alone control unit may be used to send and/or receive control instructions to and/or from detector modules. The control unit may be locally or remotely connected to the processing circuitry and the individual detector modules.

In accordance with one exemplary embodiment of the present invention, the processing circuitry may further be configured to terminate and/or interrupt the positron emission tomography event upon receiving a user-command.

The PET scanning session may also be paused, in response to a user-command. The user-command may be a pause-command or a termination-command or an interruption-command. This may allow for the user to temporarily interrupt the scan e.g. in a situation where a target organ or portion of the body is moving or is accidentally mispositioned.

In various embodiments the medical apparatus and the detector modules may operate in a networked environment using logical connections to one or more remote nodes via communication/network interfaces. The network environment may be used to send and/or receive PET scanning session data including radiation output data, ion beam data such as direction or energy of the beam, control instructions between the processing circuitry and processor units of the detector modules or data and control instructions among the detector modules. Each detector module may have a network interface or a node. The medical apparatus may have a central communication node. The remote node may be another computer, a server, a router, a peer device or other common network nodes. The communication interface may interface with a wireless network and/or a wired network. Examples of wireless networks include, for example, a BLUETOOTH network, a wireless personal area network, a wireless 802.11 local area network (LAN), and/or wireless telephony network (e.g., a cellular, PCS, or GSM network). Examples of wired networks include, for example, a LAN, a fiber optic network, a wired personal area network, a telephony network, and/or a wide area network (WAN). Such networking environments are commonplace in intranets, the Internet, offices, enterprise-wide computer networks and the like. In some embodiments, communication interface may include logic configured to support direct memory access (DMA) transfers between a memory device and other devices.

According to some embodiments, the medical apparatus may include a number of program modules and software which may be stored on a storage device, ROM or RAM, including an operating system, one or more application programs, program data, and other program modules. A user may enter commands and information into the medical apparatus through a data entry module. Data entry module may include mechanisms such as a keyboard, a touch screen, a pointing device, etc. Other external input devices may be connected to the medical apparatus via external data entry interfaces. By way of example and not limitation, external input devices may include a microphone, joystick, game pad, satellite dish, scanner, or the like. In some embodiments, external input devices may include video or audio input devices such as a video camera, a still camera, etc. Data entry module may be configured to receive input from one or more users of the device and to deliver such input to processing circuitry and/or processor units of the detector modules.

According to some examples, the program modules may have the following functions:
  prior to irradiation, the user may define the assembly configuration of the medical apparatus e.g. types of modules and how they may be geometrically configured with respect to each other.
  The program modules may receive data for estimating the positron annihilation activity at any point during the irradiation (e.g. a 3D-map of the expected isotope production distribution for each target area)
  During irradiation, the program modules may also receive progress data on the irradiation (e.g. which target area is currently irradiated)
  By combining information of expected positron annihilation activity and measured positron annihilation activity, the program modules can issue a warning when a too high (or too low) activity is measured at a certain location. Such a deviation may indicate e.g. a wrong beam penetration depth, patient mis-positioning or wrong beam shape/position. The issued warnings may be of different severities, based on user defined thresholds and tolerances.

Further, to aid the user, several other program modules or functions may be available, depending on the context of use.

Prior to operation, a program module may provide the user the possibility to define the intended assembly of the PET scanner (i.e. define the shapes of the modules to be used, and how they are to be interconnected). A hardware control of how the modules are interconnected may reduce the risk of connecting the segments in a non-intended manner.

Additional software functions in an ion beam context may also be provided:
  The data processing unit may receive information on a target point which is being irradiated and scanned.
  If the measured PET radiation representation deviates from the expected radiation representation at any point during the PET scanning, the software may issue a warning to the user.
  The warning may be in the form of an audible signal, a visible indication on a display, and/or an output signal (e.g. electrical or fiber-optical) that can be used to interrupt or terminate the PET session or ion beam irradiation.
  In case of a deviation between measured and expected PET radiation representation, the software may also produce a spatial correction that can be used as a feedback parameter to the beam delivery system for adjusting a direction or energy or orientation of the beam during the PET session.

The storage device may include a flash memory data storage device for reading from and writing to flash memory, a hard disk drive for reading from and writing to a hard disk, a magnetic disk drive for reading from or writing to a removable magnetic disk, and/or an optical disk drive for reading from or writing to a removable optical disk such as a CD ROM, DVD or other optical media. The drives and their associated computer-readable media provide nonvolatile storage of computer readable instructions, data structures, program modules and other data for the processing circuitry and/or the processor units of the detector modules. The storage device may be a plurality of distributed or centralized storage devices as well as locally or remotely accessible storage devices.

In a networked environment, program modules of the medical apparatus or portions thereof, may be stored in a remote storage device, such as, for example, on a server. It will be appreciated that other hardware and/or software to establish a communications link between the medical apparatus and other devices may be used.

In accordance with an exemplary embodiment of the present invention, the medical apparatus may further comprise at least one interconnection device, the interconnection device and the detector modules may comprise reciprocating interlocking elements configured to hold and align at least two of the detector modules. The is advantageous as it allows a flexible configuration of the scanners adapted to the measurement situation at hand. This flexible configuration is not offered by the PET-scanners used today as they are designed to have a fixed configuration when delivered from a manufacturer, which fixed configuration restricts the application areas for which PET scanning can be performed The detector modules may be joined using interconnection devices. The interconnection devices have multiple purposes, solving several mechanical and safety-related issues. The interconnection devices may have mechanical rigidity and stability to achieve a desired spatial resolution accuracy. Further, the interconnection devices may enable joining of different detector modules at different angles and orientations. The interconnection devices may realize a hardware communication bridge between different detector modules, such that each module may be able to identify its neighbor modules and information and data of the PET scanning session, orientation and position of the detector modules, etc. can be relayed by the interconnection device between the neighboring modules. This is advantageous e.g. for system assembly verification procedure, where it is verified that the actual assembly of modules corresponds to an intended setup. The interconnection devices may provide information to joint modules regarding at which angle or orientation they may be connected.

In one example, the interconnection devices may comprise a rod-like, or bar-like, rigid piece with protruding support pins/rods/bars that can be inserted and fixed in openings of detector modules. In another example the detector modules may comprise rod-like protrusions which may be inserted in openings or recesses of the interconnection devices. The reciprocating interlocking elements may be threaded connections, snap connections, nut or bolts or other interlocking mechanisms.

At least two detector modules may be attached to one interconnecting device, and the modules may be oriented at an angle e.g. at least 45, at least 90, at least 135 or at least 180 degrees with respect to each other. Additionally or alternatively, at least two detector modules may be attached to one interconnecting device, and the modules may be oriented at an angle e.g. at most 45, at most 90, at most 135 or at most 180 degrees with respect to each other. The different angular orientations of the modules may be achieved either by the engagement means of the interconnecting being positionable in different directions or by selecting a suitable interconnection device, among a plurality of interconnection devices each having differently engagement means extending in different directions.

The interconnecting device may have two connectors, one for each module, which can mate to a matching connector on the detector module. Detector module information between two attached detector modules may be relayed via the connectors. In addition, the interconnection device may supply information about the angle or orientation of the detector modules.

The interconnection device may be shaped in such a way as to allow two detector modules to be positioned or joined substantially parallel to each other, at a distance, with the two gamma-detecting sides facing each other, while permitting an ion beam to reach in between the detector modules. Further, the interconnection devices may allow the detector modules to be positioned at any orientation e.g. a U-shaped orientation (e.g. 2 flat+1 arched, or 1 U-shaped module) or a V-shaped orientation or a Pi ($\pi$)-shaped orientation.

In another example each individual gamma ray detector module may further comprise a plurality of threaded and/or non-threaded openings for mounting the individual gamma ray detector modules on a frame fixture.

The detector modules may have a plurality of fittings, abutments, studs, nuts and bolts etc. to fix the detectors on a surface or a frame. The surface may also have reciprocating receiving elements for holding and aligning the detector modules. The openings may be non-threaded for quick alignment and positioning of a module on the surface or on the frame. This way the detector modules can easily be attached to e.g. a fixed gantry of an ion beam system without interrupting the ion beam path.

In a different example, the interconnection device may further comprise an end portion rotatably mounted on an adjacent interconnection device or the frame fixture.

By this arrangement a plug and play set up can be achieved for a plurality of individual gamma ray detectors. Each detector can be easily connected to the interconnection device and the angle, orientation and spatial position of the module are adjusted. Each interconnection device may be rotated in 3D with e.g. six degrees of freedom, in up/down, back/forward, left/right, yaw, pitch, roll with respect to adjacent interconnection devices in various angles. Further, each interconnection device can be rotated with respect to a fixed frame.

In accordance with an exemplary embodiment of the present invention, each individual gamma ray detector module may have an identification code and wherein the processing circuitry and/or said processor unit may be configured to identify the gamma ray detector modules by the identification code.

The identification code may be a unique serial number for each individual gamma ray detector or may be a dynamic identification code assigned by the processing circuitry and/or the processor units during, before or after a PET scanning session. The advantage of having such identification code is that each module can be readily identified by the processing circuitry, the processor units and the interconnection devices. The interconnection devices may also comprise a processor unit or a communication unit to relay information about the connected detector modules, types or shapes of detector modules, connection sides, angles, orientation of detector modules, etc. Such information can for instance be used to confirm that the physical assembly configuration matches with the user defined assembly configuration. The advantage of dynamically assigning the identification codes by the processing circuitry is that a demand may be lifted from the user of the system to keep track of the serial numbers of the detectors while manually assembling the detectors. In other words, by using the information relayed by the interconnection devices the processing circuitry may readily identify and acquire necessary information from each connected detector module regarding the type, angle, shape, etc. during, before or after the PET session. After each module is identified a dynamic identification code can be assigned to that detector module. In another example, both a dynamic and unique serial number is used to identify the detector modules. Calibration and performance of all modules may be slightly different, so the program module or the software may require a unique serial number to know which calibration map to apply to which module. Also, the user may keep a medical record of which modules where used in each PET scanning session in order to be able to go back and check which patients underwent the PET scanning session with a particular module in case of hardware malfunctions or erroneous calibration.

In one example, the processing circuitry may further calculate a PET activity distribution of the plurality of individual gamma ray detector modules in quasi-real time based on recorded information of the positron emission tomography event.

By PET activity it is meant measured positron annihilation activity since the beginning of a PET scanning session.

In accordance with an exemplary embodiment of the present invention, the processing circuitry may further generate a warning signal when a measured PET activity at a target area in at least one portion of said animal or human body deviates from a predetermined allowed range of values.

In accordance with an exemplary embodiment of the present invention, there is provided a detector module system for positron emission tomography. The detector module system comprises a plurality of gamma ray detector modules. Each of the gamma ray detector modules is a self-contained unit comprising a housing and locking means. Further the detector module system comprises a plurality of interconnection elements wherein each of interconnection elements is a self-contained unit comprising locking means. Each pair of one detector module and one interconnection element comprises mutually engaging locking means for releasably connecting the detector module to the interconnection element. The mutually engaging locking means are further configured to releasably connecting at least two detector modules to said interconnection element. Each of said gamma ray detector modules comprises a sensor device adapted to detect gamma radiation occurring from short-lived radionuclides radiating from at least one portion of said animal or human body and to generate a radiation output corresponding to the detected gamma radiation. Further, the detector module system comprises a processing circuitry adapted to receive the radiation output from each of said gamma ray detector modules and to generate a resulting radiation representation for said positron emission tomography event, based on the received radiation output.

According to one aspect of the invention each gamma ray detector module wherein each gamma ray detector module comprises a communication interface for transfer of radiation output information from the sensor to said processing circuitry. Each sensor device further comprises a processor unit configured to generate and output said radiation output of each individual gamma ray detector module.

According to one aspect of the invention the processing circuitry is further configured to generate and send control instructions to said detector modules and/or interconnection elements to control a position and/or orientation of said detector modules.

According to one aspect of the invention each gamma ray detector module has an identification code and wherein said processing circuitry is configured to identify said gamma ray detector modules by said identification code.

According to one aspect of the invention the plurality of interconnection elements comprises a first subset of interconnection elements being configured to interconnect the detector modules at a first angle relative each other, and a second subset of interconnection elements being configured to interconnect the detector modules at a second angle relative each other, the first and second angles being selected from a range comprising at least 0, at least 10, at least 15, at least 30, at least 45 and/or at least 90 degrees in relation to each other.

According to one aspect of the invention each gamma ray detector module may comprise one or more of a fan, air inlets, power supply receiving interface, wireless communication units, electrical or optical communication interface, thermoelectric cooler or other means of temperature stabilization.

In accordance with one exemplary embodiment of the invention the medical apparatus comprises a detector module system according to any of preceding claims wherein a plurality of the detector modules are connected to each other via at least one interconnection element.

According to a third aspect of the present invention there is provided a method for monitoring of an animal or human body during a positron emission tomography event, the method comprising the steps of:
Identifying a target area on at least one portion of the animal or human body;
Positioning a first, a second and a third individual gamma ray detector module of a medical apparatus for positron e mission tomography on a respective side of the animal or human body, wherein the first and second detector modules are arranged on opposite sides of the animal or human body, and the surface normals to the first and second gamma ray detector modules are all parallel to a first geometrical plane, and at least one normal to the third gamma ray detector module is transverse to the first geometrical plane;
detecting a gamma radiation occurring from short-lived radionuclides radiating from the target area by the first and second and third individual gamma ray detector modules;
generating a radiation output corresponding to the detected gamma radiation for each of the detector modules;
receiving and generating by a processing circuitry a resulting radiation representation for the positron emission tomography event, based on the received radiation outputs.

In another example the method may further comprise the steps of:
Comparing said radiation output with a predetermined allowable range of values;
Generating in a PET scanning session, when said radiation output exceeds the allowable range of values, a warning signal to a user of the medical apparatus for positron emission tomography. In an example when the target area is irradiated with an ion beam the warning signal may also be accompanied by a control instruction from the processing circuitry or manual instructions from the user to terminate, interrupt or adjust the PET scanning session or the ion beam irradiation based on the comparison.

Effects and features of these first, second and third aspects of the present invention are largely analogous. Most embodiments mentioned above are compatible with all three aspects of the invention.

These and other features of the present invention will in the following be further clarified with reference to the embodiments described hereinafter.

BRIEF DESCRIPTION OF THE DRAWINGS

For exemplifying purposes, the invention will be described in closer detail in the following with reference to exemplary embodiments thereof illustrated in the attached drawings, wherein:

FIG. 1 is a schematic illustration of a typical ion beam setting;

FIG. 4 shows a schematic illustration of different PET/gamma ray detector modules in accordance with some embodiments of the present invention;

FIG. 5 shows a schematic illustration of a single detector module in accordance with at least one embodiment of the present invention;

FIG. 6 shows a schematic illustration of interconnection devices in accordance with at least one embodiment of the present invention;

FIG. 7 shows a schematic cross-sectional side view of a detector module in accordance with at least one embodiment of the present invention;

FIG. 8 shows a schematic cross-sectional top view of at least two detector modules in accordance with at least one embodiment of the present invention;

FIGS. 10A-B show a schematic illustration of a front view of a plurality of detector modules in accordance with at least one embodiment of the present invention;

FIG. 11 shows a schematic illustration of a PET scanner in accordance with another embodiment of the present invention;

FIG. 12 shows a schematic illustration of interconnection elements assembled with gamma ray detector modules in accordance with at least one exemplary embodiment of present invention.

FIG. 15 shows a schematic illustration of an interconnection element in accordance with at least one exemplary embodiment of the present invention.

The figures are not to scale. Generally, identical components are denoted by the same reference numerals in the figures.

DETAILED DESCRIPTION OF THE DRAWINGS

In the following detailed description, some embodiments of the present invention will be described. However, it is to be understood that features of the different embodiments are exchangeable between the embodiments and may be combined in different ways, unless anything else is specifically indicated. Even though in the following description, numerous specific details are set forth to provide a more thorough understanding of the present invention, it will be apparent to one skilled in the art that the present invention may be practiced without these specific details.

The basics and conventional techniques in electronics, sensor systems, image analysis, signal processing, data communication systems, image acquisition systems, and other components to carry out the invention are considered to be readily understood by the skilled person in the art and therefore for the sake of brevity, further explanations and details will be omitted in this description.

In other instances, well known constructions or functions are not described in detail, so as not to obscure the present invention.

Directions and extensions of the detector modules is discussed below using a Cartesian coordinate system. According to one example the first geometrical plane is parallel to the xz-plane, and the normal of the third detector module are parallel to the yz-plane. The y-direction may be parallel to the longest extension of bed, the x-direction may be parallel to the shortest extension of the bed and the z-direction may be parallel to the vertical direction.

Figure 2B:
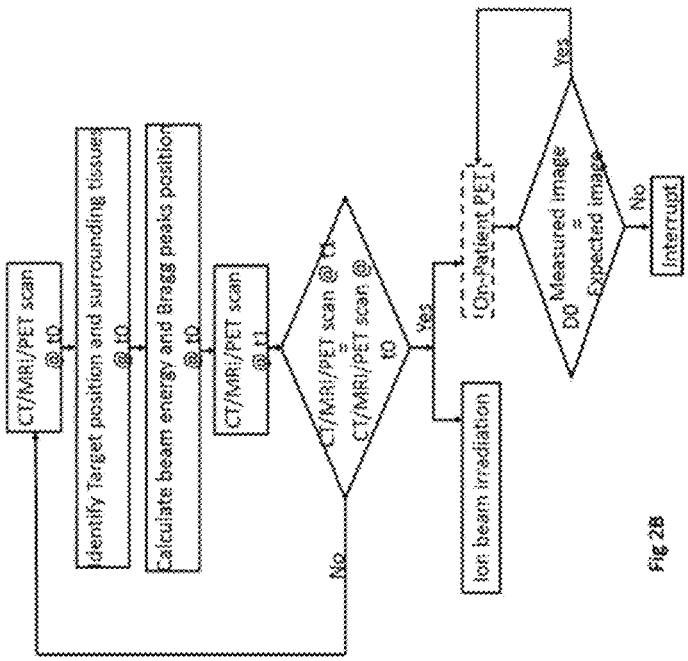
FIG. 2B is a flowchart of an ion beam irradiation preparation plan in accordance with at least one embodiment of the present invention.
Figure 2A:
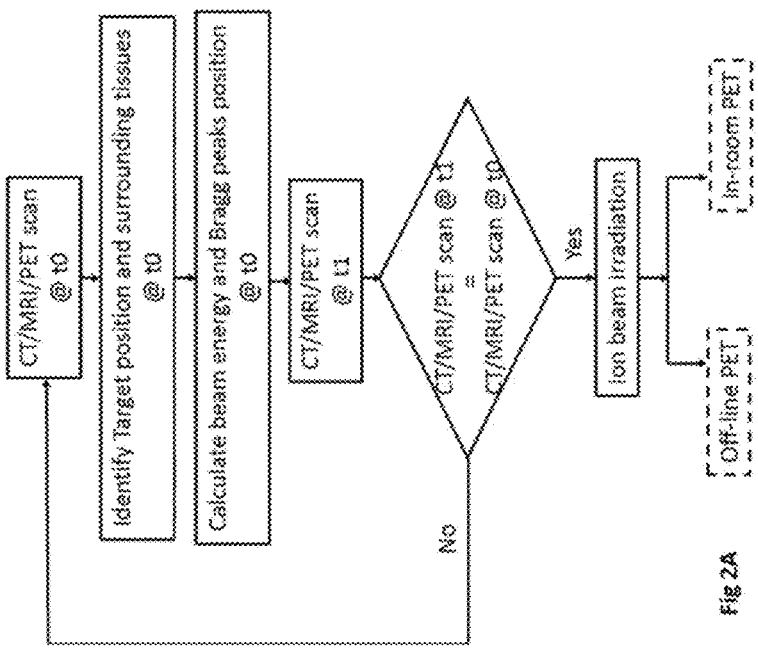
FIG. 2A is a flowchart of a conventional ion beam irradiation preparation plan.

In the following example illustrated in FIG. 1 a typical scenario involving ion beam irradiation and as illustrated in FIG. 2A an example of a conventional ion beam irradiation preparation plan for a tissue portion of a human or animal body is described. Even though in the following the principle of PET scanning according to the invention will be described in an example where the PET scanner is in operation together with an ion beam system, the skilled person will readily understand that the PET scanner according to the inventive concept can be used independently or in combination with any other imaging and/or radiation system.

Proton or heavy ion/Ion beam irradiation is one of the most precise modalities of external radiation. Unlike a photon beam which has a high entrance dose and decreases gradually while passing through the body, an ion can penetrate through tissues and deposit most of its energy near the end of its track, known as the Bragg peak.

In today's state-of-the-art ion beam systems, as illustrated in FIG. 1, the dose of irradiation is typically delivered by a narrow, typically a few mm, pencil beam 1 of a defined energy that is directed toward the patient and transversally deflected using fast ramped dipole magnets 2. The penetration depth of the beam is controlled by modulating the energy of the beam and its intensity and transverse position and size before reaching the target area is registered by beam intensity and profile monitors 3. In this manner, the tumor is "painted" in 3D. The target area may be divided into iso-energy slices 4, corresponding to the penetration depths of a given set of beam energies. Each iso-energy slice is divided into a sequence of "spots" with different transverse coordinates, where each spot shall receive a certain number of particles.

In practice, ion beam irradiation usually requires the establishment of an irradiation preparation plan as illustrated in FIG. 2A. During the preparation plan, a computer tomography (CT) scan combined with MRI/PET scan of the patient and target issues is generally performed. The CT/MRI/PET scans are used to define the position and volume of the target tissue and the surrounding tissues. The delivered dose of defined energy for the irradiation is then calculated for positioning the Bragg peak at the target spot within the target tissue. The process is normally performed several days or weeks before the actual irradiation starts indicated at time of t0 in FIG. 2A and irradiation of a patient may take several weeks distributed over several irradiation sessions. During this time period, the position and volume of the target tissue can change. Often right before each irradiation (indicated at time of t1 in FIG. 2A, a new CT scan is taken to ensure the position of target on the actual irradiation day. Since ion beam irradiation is sensitive to uncertainties compared to photon irradiation, ion range inaccuracy needs to be taken into account. However, as explained earlier using conventional off-line or in-room PET scanning approaches have drawbacks which may render the scanning process cumbersome and deliver less accurate and low resolution PET scan results.

In FIG. 2B an example ion beam irradiation preparation plan using the PET scanning for real-time monitoring of the irradiation according to an example embodiment of the present invention is illustrated.

In the inventive approach the normal procedure of identifying and acquiring necessary confirmations in steps t0 and t1 is similar to FIG. 1A. However, a real-time on-patient PET scanner monitors the irradiation process and allows the user of the system to e.g. compare the radiation representation of a PET session with the expected radiation representation in step D0.

Such real-time monitoring of the penetration depth of the ion beam can allow for feedback correction and/or beam interruption, if e.g. the measured penetration depth deviates from a planned penetration depth. In the same context, the data from the device may be used in combination with the predicted positron annihilation activity. The predicted activity can be modeled based on cross sections for different nuclear interaction between the beam and the different tissues along the beam path. By comparing the measured positron annihilation activity with the prediction, it is possible to—during irradiation and PET scanning session— detect if e.g. the actual penetration depth of the beam deviates from the planned depth.

Figure 3C:
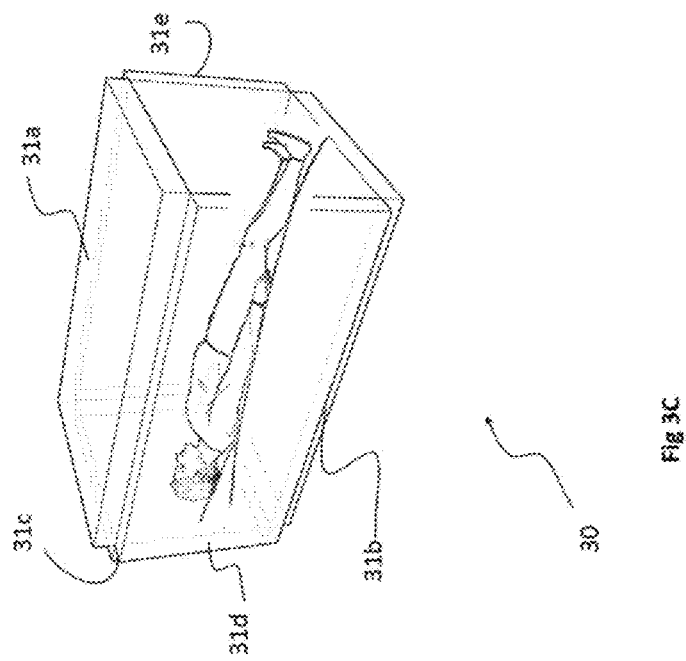
FIGS. 3A-C show schematic illustrations of arrangement of the detector modules in accordance with at least one embodiment of the present invention.
Figure 3B:
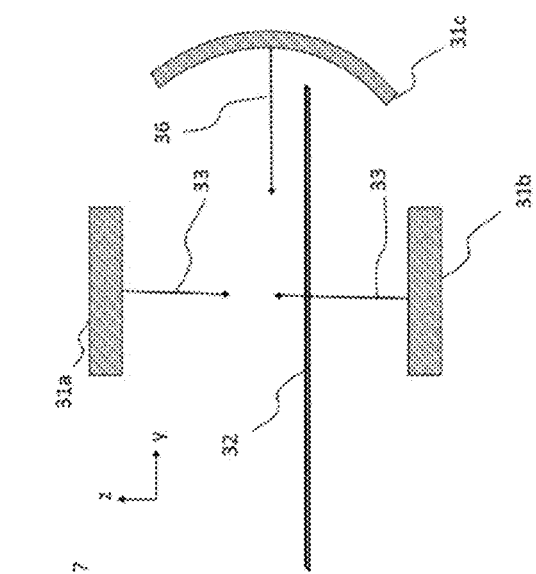
Figure 3A:
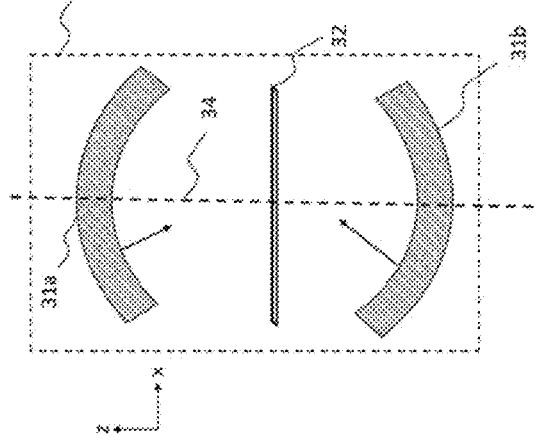

In FIG. 3A a PET scanning set up 30 is illustrated. The set up comprises a plurality of PET/gamma ray detector modules e.g. 31a, 31b, 31c arranged spatially with respect to e.g. a bed 32 where the body of a subject e.g. patient (not shown) can be placed. The detector modules 31a, 31b, 31c may be positioned in any direction, angle or orientation with respect to the bed 32. detector modules 31a, 31b, 31c may have a shape similar to the right most element 40d in FIG. 4. The modules 31a, 31b, 31c may cover only a portion or a plurality of portions of the patient's body or surround the body of the patient completely as depicted in an example of a PET scanner box 30 in FIG. 3C. Size and shape of the modules may vary based on the intended configuration for the PET session, e.g. the modules 31a, 31b, 31c, 31d, 31e in FIG. 3C may be flat module similar to module 40a or 40 b in FIG. 4 or alternatively a combination of any of the modules 40a-d. Each of the first 31a, second 31b and the third 31c detectors are placed at a distance from the patient in this example however, they can be directly placed on the patient or be embedded in the bed or couch 32 that patient is placed on. FIG. 3A is a front xz view of the PET scanner, where the first 31a and the second 31b detectors are spatially arranged in the opposite sides of a bed or couch 32. The first geometrical plane 37 is parallel to the xz-plane, and the normals of the third detector module are parallel to the yz-plane. The y-direction is parallel to the longest extension of bed, the x-direction is parallel to the shortest extension of the bed 32 and the z-direction is parallel to the vertical direction. The normals 33 of the first 31a and the second 31b detectors are parallel with the imaginary geometrical plane. The third detector 31c is arranged such that the normal 36 of the third detector 31c is transverse to the imaginary geometrical plane 37.

In FIG. 4 various examples of PET/gamma ray detector modules 40a-d for a PET scanner 30 according to the invention have been illustrated. The PET scanner system 30 may comprise several modules 40a-d of different geometrical shapes and sizes such as arched, rectangular, polygonal etc. Other examples with hemispherical, cylindrical and even irregular shapes can also be customized to the requirements of the PET session. The modules can detect gamma radiation from the decay of the radionuclide from the patient. The size i.e. any one of width 41, length 42 or depth 43 of the modules 40a-b, can be at least 100 mm or at least 200 mm or at least 300 mm or at least 400 mm or at least 500 mm. Additionally or alternatively, the size is at most 100 mm or at most 200 mm or at most 300 mm or at most 400 mm or at most 500 mm. The arched shaped modules 40d may have a central angle (also referred to as arch angle) of at least 45, at least 90, at least 120, at least 180 degrees. Additionally or alternatively, the central angle or arch angle is at most 45, at most 90, at most 120, or at most 180 degrees. Additionally or alternatively, the radius of curvature 44 of the arched modules 40d can be at least 100 mm, at least 200 mm, at least 300 mm, at least 400 mm, at least 500 mm, at least 1000 mm. Additionally or alternatively, the radius of curvature 44 of the arched modules 40d can be at most 100 mm, at most 200 mm, at most 300 mm, at most 400 mm, at most 500 mm or at most 1000 mm.

As show in FIG. 5, a detector module 31 may have a protective shell 50 which can be radiolucent at least on the side facing radiation. The module 31 may have at least one gamma-absorbing element 51, for example a scintillating crystal, in which the gamma ray is converted into an optical signal (e.g. light from the UV to near-infrared region) or an electrical signal (i.e. moving charged particles). The gamma-absorbing element 51 may be divided into multiple sub-parts, such as square "pixels" in a Cartesian grid, parallel strips or circular/hexagonal pixels in a hexagonal grid, such that information about which sub-part of the module the gamma ray was absorbed in gives information on the spatial coordinates where the gamma ray entered the module. If the module has multiple scintillating crystals as gamma-absorbing elements, it may have multiple photon detectors 52 e.g. photomultipliers (PMTs) or silicon photomultipliers (SiPMs) that are optically connected to the crystals 51 in order to convert the secondary light generated by the gamma ray into an electrical signal.

The module may alternatively have electro-optical light guides (not shown) for incoming coherent light that may be used to detect the presence of secondary electrons.

Each module 31 may also comprise a processor unit 53. The processor unit 53 may transmit data by a wired or wireless data transmitter and/or receiver 54 on detected events to a local or remote processing circuitry (not shown) electrically, optically or wirelessly.

The processor unit 53 is employed e.g. for operating data processing and or communicating data, control instruction, etc. with the processing circuitry, or other detector modules 31 locally or remotely via the communication transmitter and/or receiver 54. The processor unit 53 or additionally or alternatively the processing circuitry may convert the electrical signal from the detectors (e.g. PMTs or SiPMs) into digital information about the event, such as a time-stamp (time of the event), energy (number of photons detected) and coordinates of the event. The readout unit may have the capability to veto (ignore) events that do not fit certain criteria (e.g. too low signal).

The module may have optical fibers or other light guides (not shown) that directly guides the light generated in the gamma absorbing elements 51 (e.g. Cherenkov radiation from secondary electrons) to photon detectors 52 inside or outside the module 31.

The module may have other or additional means to convert the absorption of a gamma ray into an informative signal than merely detection of scintillating light. This could, for example, be a Cherenkov radiation medium, where secondary electrons of sufficiently high kinetic energy, created via gamma absorption, generate light in the visible and UV range. This light could be detected inside the module 31, similarly to scintillating light.

The internal components of the module may be contained in the protective shell 50, which may have multiple functions: to protect the internal components from external forces (e.g. during handling or assembly); to insulate the exterior environment from any high-voltage fields present inside or to incorporate mechanisms to attach one module to another such as openings, recesses, electrical connections etc.

The shell 50 may have clearly visible markings from which the gross dimensions of the module, as well as the dimensions of the gamma-ray absorbing parts, can be inferred (e.g. a type code and/or actual dimensions).

The shell 50 may be of a rectangular shape, or an arched shape, a hemispherical shape or other polygonal shapes, as indicated in FIG. 4. The shell 50 may also have any other symmetrical or asymmetrical or even irregular shapes. This can be particularly advantageous to fit the detectors to parts or target areas with difficult access points on the body of a patient or animal.

The sides or back of the shell 50 can be equipped with connective mechanisms by which two modules can be connected. Additionally or alternatively they may be connected by separate mechanism such as screws. The sides or back of the shell 50 may be equipped with identifying markers such that it is possible to infer the types of neighbouring modules a module has been connected to. The neighbour-identifying mechanism may, for example, include a pattern of pins that is unique for each different module shape (not shown)

The shell 50 may have an input for connecting power (not shown) to any electronic equipment inside the shell 50 (e.g. wireless transmitter and/or detectors).

A module 31 may be connected to several other modules 31 in customizable layouts and from multiple sides of each module to form expandable modular detector connections. This is particularly advantageous to create completely modular arrays of the detectors 31 which can be customized for particular body parts or PET sessions. The connected detectors can be easily disassembled and reassembled for different PET scan events.

In one example, the modules 31 may be joined by use of interconnection devices 60, 61 of different shapes and types, as illustrated in FIG. 6. The modules 31 can be joined e.g. at 90 degrees relative each other using the interconnection device 60 or at 180 degrees using interconnection device 61.

In general, the different angular orientations of the modules may be achieved either by the engagement means of the interconnecting being positionable in different directions or by selecting a suitable interconnection device, among a plurality of interconnection devices each having engagement means extending in different directions and thereby providing for different angular orientations of the modules.

The interconnection devices 60, 61 may relay information between neighbouring modules and provide structural rigidity to the connected modules. The interconnection devices have reciprocating interlocking elements e.g. rods, pins, etc. In this implementation, the interconnection devices 60, 61 include rod-like or bar-like, rigid pieces with protruding support pins/rods 62 and/or male or female interconnection connectors/pins 63. Two detector modules may be attached to one interconnection device 60, 61. Additionally or alternatively, the protruding parts may be located on the detector modules 31 and reciprocating receiving openings or recesses be located on the interconnection devices.

An interconnection device 60, 61 may have a type-unique pin-pattern to relay information to the two detector modules it connects about the angle, orientation or direction of the connected modules.

In in FIG. 11-15 one exemplary embodiment is shown of a detector module system for positron emission tomography. The detector module system 100 comprises a plurality of gamma ray detector modules 101. Each of the gamma ray detector modules is a self-contained unit comprising a housing 102. As each of the gamma ray detector modules are capsuled by the housing 102, each of the gamma ray detector modules fulfils certification standards for use within hospitals.

Each pair of one detector module 101 and one interconnection element comprises mutually engaging locking means 104 for releasably connecting the gamma ray detector module 101 to the interconnection element 103. Each mutually engaging locking means 104 comprises a male and a female mutually engaging locking means. Further, each interconnection element comprises locking means 105 for releasably connecting at least two detector modules 101 to the interconnection element 103. Each of the interconnection elements is a self-contained unit comprising locking means.

Further, each of said gamma ray detector modules 101 comprises a sensor adapted to detect gamma radiation occurring from short-lived radionuclides radiating from at least one portion of said animal or human body and to generate a radiation output corresponding to the detected gamma radiation.

Further the detector module system comprises a processing circuitry adapted to receive said radiation output from each of said individual gamma ray detector modules and to generate a resulting radiation representation for said positron emission tomography event, based on said received radiation output.

Further, each gamma ray detector module 101 may comprise a communication interface for transfer of radiation output information from the sensor within the gamma ray detector module. And the detector module system 100 comprises an interface to receive radiation output information from the gamma ray detector modules.

Each gamma ray detector module further comprises a processor unit configured to generate and send the radiation output of each individual gamma ray detector module to the processing circuitry. Further, the processing circuitry is further configured to generate and send control instructions to the detector modules 101 to control a position and/or orientation of the detector modules 101.

Each gamma ray detector module has an identification code and wherein the processing circuitry and/or the processor unit are configured to identify said gamma ray detector modules 101 by the identification code.

The gamma ray detector modules 31 may be joined with e.g. 0, 10, 15, 30, 45 or 90 degrees or any other angular relationship in relation to each other. The interconnection element 103 comprises locking means formed as rods, pins, plates etc. The interconnection element 103 may also be referred to as interconnection device in this description. At least two gamma ray detector modules 101 may be joined with an inclined relation in relation to each other. Further, the interconnection element 103 is attached to one of the gamma ray detector modules 101 by means of the locking means 105. In the event the modules 101 are to be inclined in relation to each other, the locking means 105 of the interconnection element 103 may be inclined in relation to each other such that the gamma ray detector modules 101 may be inclined in relation to each other. The locking means 105 may be two or more on each interconnection element 103, thus sufficient to assemble two gamma ray detector modules 101 in relation to each other. Further, the interconnection element 103 may be designed such that the gamma ray detector modules 101 may be inclined 10, 15, 30, 45 or 90 degrees in relation to each other.

Further, the interconnection element 103 may comprise mutually engaging locking means for releasably connecting the detector module to the interconnection element 103. Further, each interconnection element 103 comprises and locking means for releasably connecting at least two detector modules 101 to the interconnection element 103.

When two modules 101 are arranged to be joined with e.g. 0 degrees in relation to each other, the interconnection element 103 may be shaped as a plate, shown in FIG. 15, arranged between two gamma ray detector modules 101.

An assembly of a plurality of gamma ray detector modules 101 and one or more interconnecting elements 103 may form different geometrical shapes, such as concentric ring, sphere, ring, square box etc.

Further, two gamma ray detector modules 101 may be joined even though they are not joined in the vicinity of each other, i.e. the gamma ray detector modules are not directly neighbouring with each other. In other words, two gamma ray detector modules may be assembled at a distance from each other. Thus, an opening may be formed between two gamma ray detector modules such that an ion beam may pass unobstructed.

The locking means may be attached to the gamma ray detector modules by means of attachment means such as e.g. screws or bolts or other suitable means, as shown in FIG. 12.

Further, the inclination angle between the various modules may be equal or different in relation to each other. FIG. 15 shows one example of an interconnection element for joining two modules inclined 0 degrees in relation to each other, and FIG. 12 shows one example of two modules inclined 45 degrees to each other.

The overall design of the interconnection elements enable the modules 101 to be assembled without a supporting frame i.e. the assembled modules are self-supported or self-contained by means of the interconnection elements 103 and their housings 102. The gamma ray detector modules may also be integrated with a patient table or similar equipment.

As shown in FIG. 12 each of the gamma ray detector modules 101 is encapsulated by a housing, whereupon the interconnection elements 103 are adapted to be attached. Each gamma ray detector module may comprise a fan 107 and air inlets 108. This is to be able to control the temperature within the module. Further, the gamma ray detector modules may comprise one or more of a power supply interface, wireless communication units.

The mutually engaging locking means 104 are provided to allow identification between two adjacent modules, such that processing circuitry may retrieve information regarding the characteristics of the connected modules. Examples of such characteristics may be size, inclination, quantity, position in relation to another module, ID-information among some.

Figure 14:
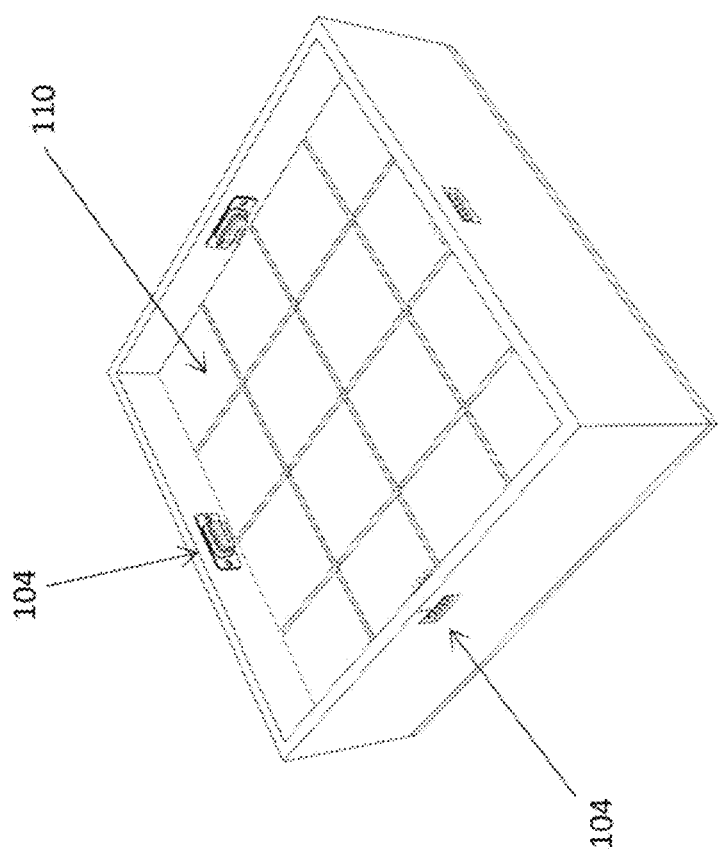
FIG. 14 shows a schematic illustration of the interior of a gamma ray detector module in accordance with at least one exemplary embodiment of present invention.
Figure 13:
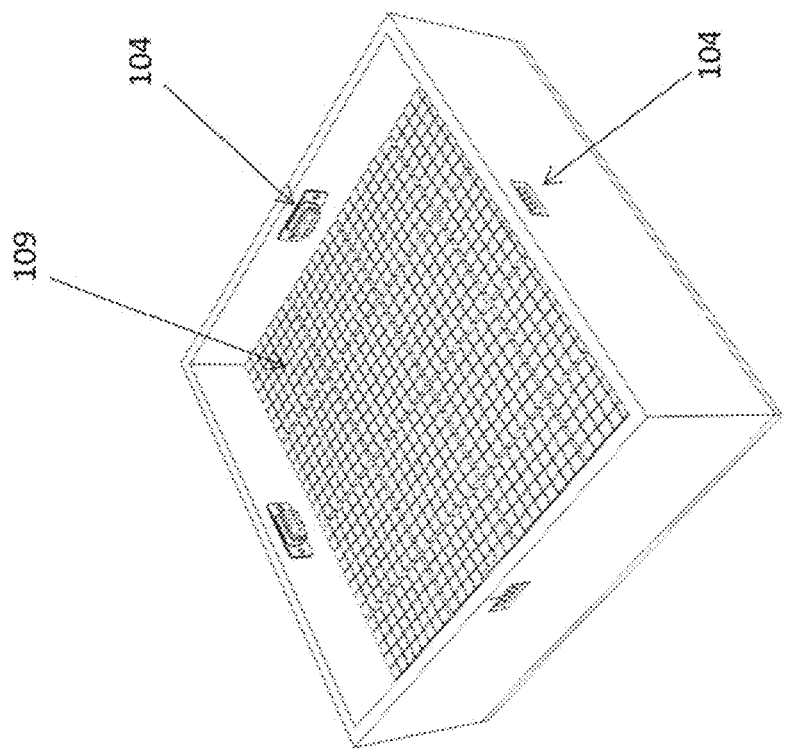
FIG. 13 shows a schematic illustration of the interior of a gamma ray detector module in accordance with at least one exemplary embodiment of present invention.

As shown in FIG. 13-14, within the interior of the module there is provided crystal arrays 109. Adjacent to the crystal arrays there is arranged silicon photomultiplier arrays 110. Further, the receiving means are adapted to be connected to inter alia the crystal arrays and the silicon photomultiplier arrays.

The gamma ray detector modules may be assembled and configured in different configurations depending on the requirements for the PET-scanning session. Thus, how many and the inclination of the modules in relation to each other may be determined by which body part of a patient that is to be treated within the PET scanning session. Thus, the modules are reconfigurable and may be manually assembled in different configurations on site for the PET-scanning session. If a larger field of view or increased sensitivity is needed one or more modules are just simply added to the already existing module(s). In the case, a smaller field of view or decreased sensitivity is needed one or more modules are just simply removed from the already existing module (s). In other words, the assembled modules of the PET-scanner may be assembled dependent on human input from the operator of the PET-scanner at the site for the PET scanner session.

FIG. 7 illustrates a cross-sectional side view of a detector module 31 taken along the line 81 in FIG. 8.

In this example there are two holes 71 for attaching an interconnection device. In the center, a female connector 72 into which the interconnection connector (e.g. male pins) is connected is arranged. In this example the interconnection connector 72 has three groups of pins:

1—Support ID 73: One of the female connector pins of the module has +5V, another one is GND. Inside the interconnection device, a number of male pins are electrically connected to the +5 V, the other ones to GND. Which pins are connected to +5 V or GND depends on the interconnection device type (e.g. 90 degrees or 180 degrees). Upon joining the module and the support, the module can detect which of the support pins have a +5 voltage, and thus identify which type of support has been connected on which side.

2—NEIGHB IN 74: Each detector module can output a type-unique pin pattern of GND/+5 V on the central group of pins. This pattern is forwarded by and through the interconnection device to the neighbor module, such that each module can detect which type of module it is connected to, on all sides (neighbor recognition). Other implementations for neighbor recognition based on information transmission between the neighboring modules are of course conceivable for the person skilled in the art. For instance, Other means of neighbor recognition could be RFID-tags, barcode reading, magnetic N/S pattern, etc. Modules may also be equipped with e.g. accelerometers to verify their angle or orientation in space.

3—NEIGHB OUT 75: A type-unique pattern of GND/+ 5V module output pins that may be forwarded to a neighbor module.

FIG. 8 illustrates an example of two different types of detector modules, type "C" and "B", joined with an interconnection device type 180. The detector module side not facing radiation 82 has sets of threaded holes 83 at fixed distances that may be used to fix the module e.g. on a vertical surface. Another set of non-threaded holes 84 may be used to quickly align and position a module by placing it on top of a surface (e.g. a patient table/couch), where protruding studs at corresponding distances maintain the position of the module. In this example the width 85 of the module C is 400 mm and the length 86 of module C is 400 mm. Width of module B is 200 mm and length of module B is 400 mm.

Figure 9:
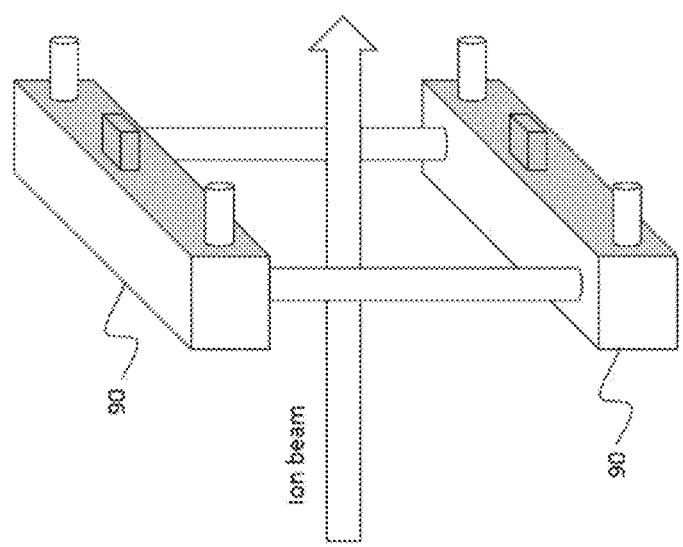
FIG. 9 shows a schematic side view of a pair of interconnection devices in accordance with at least one embodiment of the present invention.

FIG. 9 illustrates an interconnection device 90 for mounting two parallel detector modules (not shown) at a distance, with an opening for an ion beam to pass unobstructed.

FIG. 10A illustrates an example where the detector module 31 e.g. three identical 120 degree arched modules 31 can be placed directly on one side of the subject e.g. under the patient. The preassembled modules 31 can be arranged and moved manually by the user or controlled remotely by a remote-control instruction generated by the processing circuitry. The modules can be moved to desired positions e.g. depending on the direction of the ion beam during the irradiation and efficiently cover full-ring solid angles as shown in FIG. 10B.

FIG. 11 illustrates different sizes of PET detector modules 31 that can be used on animals 110 with different sizes. Several modules can be assembled to cover a larger surface or disclose the entire animal body in order to complete a whole body PET scan.

The skilled person in the art realizes that the present invention by no means is limited to the embodiments described above. The features of the described embodiments may be combined in different ways, and many modifications and variations are possible within the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements.

Itemized List of Embodiments

Item 1. A medical apparatus for positron emission tomography, said medical apparatus comprising:
a plurality of individual gamma ray detector modules, wherein said plurality of individual gamma ray detector modules comprises a first, a second and a third gamma ray detector module each of said first second and third gamma ray detector modules being adapted to be arranged on a respective side of an animal or human body during a positron emission tomography event, and each of said modules being adapted to detect gamma radiation occurring from short-lived radionuclides radiating from at least one portion of said animal or human body and to generate a radiation output corresponding to the detected gamma radiation, wherein said first and second detector modules are arranged on opposite sides of said animal or human body, and the surface normals to said first and second gamma ray detector modules are all parallel to a first geometrical plane, and at least one normal to said third gamma ray detector module is transverse to said first geometrical plane;

a processing circuitry adapted to receive said radiation output from each of said individual gamma ray detector modules and to generate a resulting radiation representation for said positron emission tomography event, based on said received radiation output.

Item 2. The medical apparatus according to item 1, wherein each individual gamma ray detector module further comprises a processor unit configured to generate and send said radiation output of each individual gamma ray detector module to said processing circuitry.

Item 3. The medical apparatus according to any one of preceding items, wherein said processing circuitry is further configured to generate and send control instructions to said detector modules to control a position and/or orientation of said detector modules.

Item 4. The medical apparatus according to any one of preceding items, wherein said control instructions further comprise a deactivation instruction to deactivate functionality of at least one of said plurality of individual gamma ray detector modules during said positron emission tomography event.

Item 5. The medical apparatus according to any one of the preceding items, wherein said processing circuitry is further configured to terminate and/or interrupt the positron emission tomography event upon receiving a user-command.

Item 6. The medical apparatus according to any one of preceding items, wherein the medical apparatus further comprises at least one interconnection device, said interconnection device and said detector modules comprise reciprocating interlocking elements configured to hold and align at least two of said detector modules.

Item 7. The medical apparatus according to any one of preceding items, wherein each individual gamma ray detector module has an identification code and wherein said processing circuitry and/or said processor unit are configured to identify said gamma ray detector modules by said identification code.

Item 8. The medical apparatus according to any one of the preceding items, wherein said processing circuitry further generates a warning signal when a measured PET activity at a target area in the at least one portion of said animal or human body deviates from a predetermined allowed range of values.

Item 9. A method for monitoring of an animal or human body during a positron emission tomography event, said method comprising the steps of:

Identifying a target area on at least one portion of said animal or human body;

Positioning a first, a second and a third individual gamma ray detector module on a respective side of the animal or human body, wherein said first and second detector modules are arranged on opposite sides of said animal or human body, and the surface normals to said first and second gamma ray detector modules are all parallel to one geometrical plane, and at least one normal to said third gamma ray detector module is transverse to said geometrical plane;

Detecting a gamma radiation occurring from short-lived radionuclides radiating from said target area by said first and second and third individual gamma ray detector modules;

Generating a radiation output corresponding to the detected gamma radiation for each of said detector modules;

Receiving and generating by a processing circuitry a resulting radiation representation for said positron emission tomography event, based on said received radiation outputs.

The invention claimed is:

1. A detector module system for positron emission tomography, said detector module system comprising:
 a plurality of gamma ray detector modules,
 each of the gamma ray detector modules is a self-contained unit comprising a housing and locking means,
  a plurality of interconnection elements wherein each of the interconnection elements is a self-contained unit comprising locking means,
 wherein
 each pair of one detector module and one interconnection element comprises mutually engaging locking means for releasably connecting the detector module to the interconnection element
  wherein said mutually engaging locking means are further configured to releasably connecting at least two detector modules to said interconnection element
  each of said gamma ray detector modules comprises a sensor device adapted to detect gamma radiation occurring from short-lived radionuclides radiating from at least one portion of said animal or human body and to generate a radiation output corresponding to the detected gamma radiation, wherein
  a processing circuitry adapted to receive said radiation output from each of said gamma ray detector modules and to generate a resulting radiation representation for said positron emission tomography event, based on said received radiation output, wherein said plurality of interconnection elements comprises a first subset of interconnection elements being configured to interconnect said detector modules at a first angle relative each other, and a second subset of interconnection elements being configured to interconnect said detector modules at a second angle relative each other, wherein said first angle is different from said second angle,
  each of said gamma ray detector modules comprises a processor unit configured to generate and send the respective radiation output of each individual gamma ray detector module to the processing circuitry and configured to send the respective spatial position or angle of each individual gamma ray detector module to the processing circuitry or to the processor units of the other individual gamma ray detector modules
  said processing circuitry is further adapted to receive information on how the different modules are oriented in space from said gamma ray detector modules and to generate said resulting radiation representation based on said information
  so as to enable the spatial position, orientation, angles and directions of the detector modules to be adjusted and changed in a manual or automated way by the user during, before or after said positron emission tomography event.

2. The detector module system according to claim 1, wherein said first and second angles being selected from a range comprising 0 and/or at least 90 degrees in relation to each other.

3. The detector module system according to claim 1, wherein each gamma ray detector module comprises a communication interface for transfer of radiation output information from said sensor to said processing circuitry.

4. A detector module system according to claim 1, wherein each sensor device further comprises a processor unit configured to generate and output said radiation output of each individual gamma ray detector module.

5. A detector module system according to claim 1, wherein said processing circuitry is further configured to generate and send control instructions to said detector modules and/or interconnection elements to control a position and/or orientation of said detector modules.

6. Detector module system according to claim 1, wherein each gamma ray detector module has an identification code and wherein said processing circuitry is configured to identify said gamma ray detector modules by said identification code, said identification code together with information about orientation and position of the gamma ray detector modules are relayed by the interconnection elements between neighboring gamma ray detector modules.

7. The detector module system according to claim 1, wherein each gamma ray detector module may comprise one or more of a temperature stabilizing element, air inlets, power supply receiving interface, wireless communication units, electrical communication interface, optical communication interface.

8. A medical apparatus for positron emission tomography, said medical apparatus comprising a detector module system according to claim 1, wherein a plurality of said detector modules are connected to each other via at least one interconnection element.

* * * * *